United States Patent
Pelati et al.

(10) Patent No.: US 8,648,007 B2
(45) Date of Patent: Feb. 11, 2014

(54) VAPORIZATION AND TRANSPORTATION OF ALKALI METAL SALTS

(75) Inventors: Joseph E. Pelati, Houston, TX (US); James R. Butler, League City, TX (US); Hollie Craig, Seabrook, TX (US)

(73) Assignee: Fina Technology, Inc., Houston, TX (US)

( * ) Notice: Subject to any disclaimer, the term of this patent is extended or adjusted under 35 U.S.C. 154(b) by 887 days.

(21) Appl. No.: 12/685,892

(22) Filed: Jan. 12, 2010

(65) Prior Publication Data

US 2011/0172480 A1    Jul. 14, 2011
US 2013/0165722 A9    Jun. 27, 2013

Related U.S. Application Data

(63) Continuation-in-part of application No. 12/107,748, filed on Apr. 22, 2008.

(51) Int. Cl.
    *B01J 20/34*  (2006.01)
(52) U.S. Cl.
    USPC .......... 502/344; 502/53; 502/55; 502/24; 502/25; 502/34
(58) Field of Classification Search
    USPC ........................................................ 585/12
    See application file for complete search history.

(56) References Cited

U.S. PATENT DOCUMENTS

| | | | |
|---|---|---|---|
| 4,590,324 A | 5/1986 | Satek | |
| 4,633,909 A * | 1/1987 | Louboutin et al. | 137/888 |
| 5,503,163 A | 4/1996 | Boyd | |
| 5,686,369 A * | 11/1997 | Chen et al. | 502/25 |
| 5,689,023 A | 11/1997 | Hamilton | |
| 5,689,027 A | 11/1997 | Abichandani et al. | |
| 5,739,071 A | 4/1998 | Chen et al. | |
| 6,184,174 B1 | 2/2001 | Rubini et al. | |
| 6,936,743 B2 | 8/2005 | Butler | |
| 2009/0264278 A1* | 10/2009 | Butler et al. | 502/34 |

FOREIGN PATENT DOCUMENTS

CN    1126986 A    7/1996
CN    101124183 A    2/2008

OTHER PUBLICATIONS

Office Action issued in Chinese Patent Appliction No. 201180005667.5, dated Nov. 5, 2013 and English translation thereof (20 pages).
English Abstract of CN1126986A from Patent Espacenet, publication date Jul. 17, 1996 (2 pages).
English Abstract of CN101124183A from Patent Espacenet, publication date Feb. 13, 2008 (1 page).

* cited by examiner

*Primary Examiner* — Melvin C Mayes
*Assistant Examiner* — Colette Nguyen

(57) ABSTRACT

An apparatus and method for vaporizing and transporting an alkali metal salt is shown. The apparatus has a first conduit capable of transporting an alkali metal salt solution and a second conduit in fluid communication with the first conduit, the second conduit capable of transporting steam so that the alkali metal salt is dissipated into the steam forming a solution that can be transported, such as to a remote reaction zone. The solution can be transported via a third conduit that is capable of being heated by a heat source. The method can be used to add a promoter to a dehydrogenation catalyst during a dehydrogenation reaction.

23 Claims, 5 Drawing Sheets

VAPORIZATION AND TRANSPORTATION OF ALKALI METAL SALTS

CROSS-REFERENCE TO RELATED APPLICATIONS

This application is a continuation in part of U.S. patent application Ser. No. 12/107,748, which was filed on Apr. 22, 2008.

FIELD

The present invention generally relates to catalytic dehydrogenation reactions. More specifically, this invention relates to the dehydrogenation of alkyl aromatic compounds to produce vinyl aromatic compounds.

BACKGROUND

Catalytic dehydrogenation processes are well known in the art. Such processes include the dehydrogenation of an alkyl aromatic compound to yield a corresponding alkenyl aromatic compound, and the dehydrogenation of a mono-olefin to yield a corresponding conjugated di-olefin. A specific example of catalytic dehydrogenation is the commonly used process to produce styrene, a vinyl aromatic compound, by the catalytic dehydrogenation of ethylbenzene.

Many known dehydrogenation catalysts and operating parameters each have unique advantages and disadvantages. There are a number of factors to consider relative to a dehydrogenation catalyst and their particular operation, such as for example between the level of conversion and the useful catalyst life. Catalyst life is an important consideration in dehydrogenation reactions. There are the costs related to the catalyst itself, such as the unit cost of the catalyst, the useful life of the catalyst, the ability to regenerate used catalyst, and the cost of disposing of used catalyst. There are also the costs related to shutting down a dehydrogenation reactor to replace the catalyst and/or to regenerate the catalyst bed, which includes labor, materials, and loss of productivity.

Normal catalyst deactivation can tend to reduce the level of conversion, the level of selectivity, or both, each which can result in an undesirable loss of process efficiency. There can be various reasons for deactivation of dehydrogenation catalysts. These can include the plugging of catalyst surfaces, such as by coke or tars, which can be referred to as carbonization; the physical breakdown of the catalyst structure; and the loss of promoters, such as the physical loss of an alkali metal compound from the catalyst. Depending upon the catalyst and the various operating parameters that are used, one or more of these mechanisms may apply.

It is generally preferred to maximize the useful catalyst life, and there are a number of techniques or methods that are known. One technique that is sometimes employed is to raise the reaction temperature. This can be accomplished, for example, by increasing the temperature of the reactant stream or by adding heat to the reactor chamber. Such a reaction temperature increase will generally increase the rate of reaction, which can offset the deactivation of the catalyst, but may also have undesirable results such as harming efficiency or selectivity. There can also be narrow limits to the utility of this temperature-raising technique. There may also be a mechanical temperature limit of the catalyst or the equipment, beyond which further temperature increases can degrade the catalyst's physical structure and/or the equipment's integrity. As this limit is approached, the catalyst would then need to be either replaced or regenerated by conventional ways. Conventional practice generally involves shutting down the reactor and physically removing the catalyst for replacement.

It would be desirable to have a catalyst regeneration method that could be used during steady-state process conditions without process interruption, which would maintain acceptable levels of conversion and selectivity. It is also desirable to have an apparatus to facilitate the addition of the catalyst life extender to the process during steady-state process conditions. It is also desirable to have an apparatus to facilitate the addition of the catalyst life extender to multiple processes simultaneously. Furthermore, it is desirable to transport the catalyst life extender from a remote location.

SUMMARY

One embodiment of the present invention is an apparatus for vaporizing an alkali metal salt into steam having a first conduit capable of transporting an alkali metal salt solution, the first conduit having at least one opening through which the solution can exit the first conduit. A second conduit is in fluid communication with the first conduit. The second conduit is capable of transporting a stream that includes steam. The alkali metal salt solution is injected concurrently into the steam forming a solution of alkali metal salt in steam. The solution of alkali metal salt in steam is thereafter transported in a third conduit that is in fluid communication with the second conduit, wherein the third conduit is capable of being heated by a heat source, such as a steam jacket.

In an embodiment, the apparatus has at least one diffuser located adjacent to the opening of the first conduit to dissipate the alkali metal salt solution into the steam. The third conduit can be connected to a fourth conduit for transporting the vaporized alkali metal salt in steam into a stream within the fourth conduit. The stream located within the fourth conduit can also contain reactants for a dehydrogenation reaction of an alkyl aromatic hydrocarbon. The apparatus may further have a weir located adjacent to the connection to the fourth conduit to restrict the flow of any of the alkali metal that is not dissipated into the steam from entering the third conduit. The portion of the second conduit containing the opening of the first conduit can form a mixing chamber wherein the alkali metal stream can be dissipated into the steam to form a third stream prior to the third stream entering the third conduit. The mixing chamber portion of the second conduit can be capable of being heated by a heat source, such as a steam jacket. A portion of the first conduit can be disposed within the second conduit in a substantially concentric arrangement. The alkali metal salt can be added as a solid, liquid, or a vapor, or a combination thereof.

Another embodiment concerns a method of enhancing the activity of a dehydrogenation catalyst promoted with an alkali metal, during a catalytic dehydrogenation reaction. The method includes forming a first solution by adding an alkali metal salt to steam utilizing an apparatus for adding the alkali metal salt into the steam. The apparatus has a first conduit capable of transporting a first stream of the alkali metal salt, the first conduit having at least one opening through which the first stream can exit the first conduit. A second conduit is in fluid communication with the first conduit; wherein the second conduit is capable of transporting a second stream that can include steam. The first stream exits the first conduit and, in the second conduit, is subjected to a heat source and simultaneously dissipated into the second stream forming the first solution containing alkali metal salt of the first stream in solution with the steam of the second stream. The first solution exists the second conduit and enters a third conduit in fluid communication with the second conduit. In the third conduit, the first solution is further heated and transported to a fourth conduit. In the fourth conduit, the first solution is brought into contact with the dehydrogenation catalyst.

The third conduit is subjected to a heat source that supplies heat to the first solution as it is transported to the fourth conduit. The third conduit can be subject to an amount of heat sufficient to maintain the first solution at temperatures between 150 and 500° C. In an aspect, the third conduit serves to transport the first solution from the second conduit to the fourth conduit, located at a remote location. The third conduit is also subject to an amount of heat sufficient to maintain the first solution in a pumpable state.

The alkali metal salt can be added in amounts sufficient to maintain substantially constant levels of catalyst activity, and in an aspect is a potassium salt compound. The catalytic dehydrogenation reaction can be the dehydrogenation of an alkyl aromatic hydrocarbon reactant stream to obtain an alkenyl aromatic hydrocarbon. The alkali metal salt can be added to the steam stream as a solid, liquid, or vapor, or a combination thereof. In an embodiment, the catalyst contains 40-80 wt % iron oxide and 5-30 wt % of an alkali metal compound. The alkali metal salt can be added in amounts equivalent to a continuous addition of 0.01 to 1000 parts per million by weight of alkali metal relative to the weight of the total reactant stream. In an embodiment, the alkyl aromatic hydrocarbon is ethylbenzene and the alkenyl aromatic hydrocarbon is styrene.

Yet another embodiment is a method of vaporizing and transporting an alkali metal salt. The method involves providing a first stream including alkali metal salt into a first conduit capable of transporting an alkali metal salt, the first conduit having at least one opening through which the alkali metal salt can exit the first conduit. A second stream that includes steam is provided to a second conduit that is in fluid communication with the first conduit and capable of transporting a steam input stream. As the alkali metal salt exits the first conduit it is heated and simultaneously dissipated into the steam input stream forming a third stream containing vaporized alkali metal salt in solution with the steam. The portion of the first conduit containing the opening can be disposed within the second conduit in a substantially concentric arrangement. There can be at least one diffuser located adjacent to the opening of the first conduit to dissipate the first stream into the second stream. The third stream is sent to a third conduit in fluid communication with the second conduit. The third conduit is subject to a heat source. The third conduit may be connected to a fourth conduit for transporting the third stream into contact with a fourth stream within the fourth conduit and can further include a weir located adjacent to the connection of the third conduit to the fourth conduit to restrict the flow of any of the alkali metal that is not dissipated into the second stream from entering the fourth conduit.

Still another embodiment is an apparatus for supplying a potassium carboxylate catalyst life extender to a reaction chamber loaded with an iron oxide based, alkali metal promoted, dehydrogenation catalyst used to prepare a vinyl aromatic hydrocarbon from a feed stream including an alkyl aromatic hydrocarbon. The apparatus has a first conduit capable of transporting a first stream of a potassium carboxylate, the first conduit having at least one opening through which the first stream can exit the first conduit. At least a portion of the first conduit containing the at least one opening is disposed within a second conduit capable of transporting a second stream that can include steam. As the first stream exits the first conduit it is heated and simultaneously dissipated into the second stream forming a third stream containing vaporized potassium carboxylate of the first stream in solution with the steam of the second stream. The third stream containing vaporized potassium carboxylate in solution with steam is thereafter transported in a third conduit that is connected to the second conduit, wherein the third conduit is connected to a heat source.

DETAILED DESCRIPTION

Figure 1:
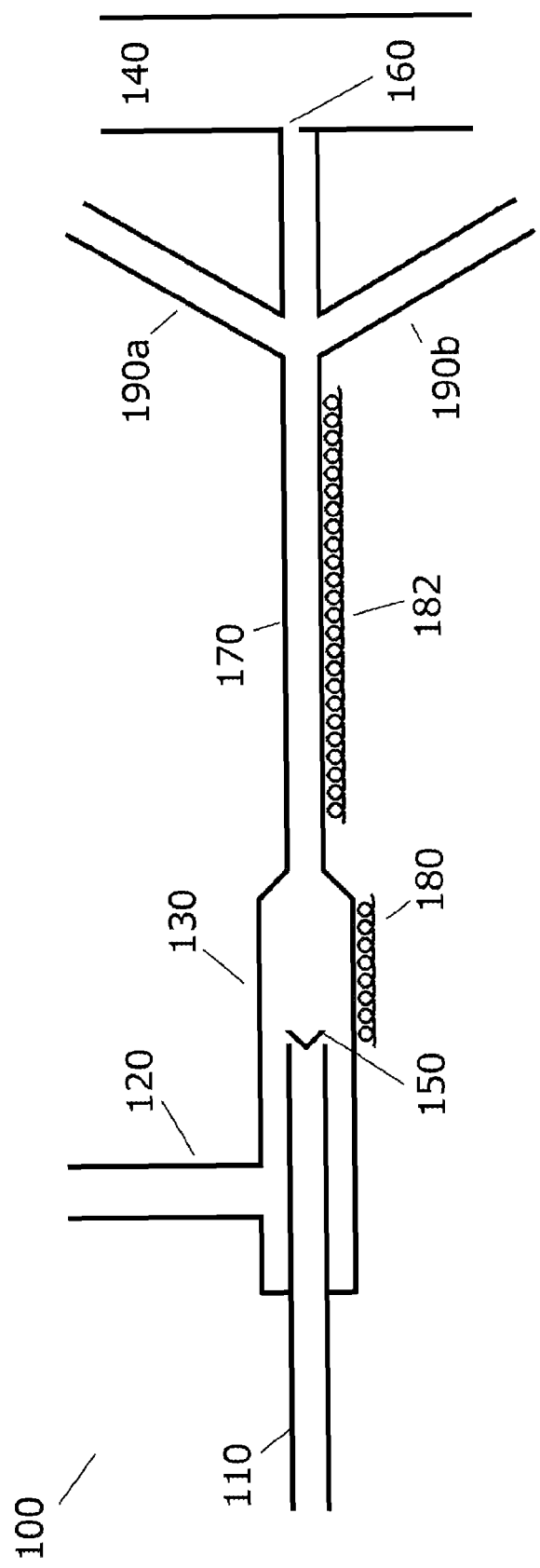
FIG. 1 illustrates an embodiment of the apparatus of the present invention for vaporizing an alkali metal salt into steam.
Figure 2:
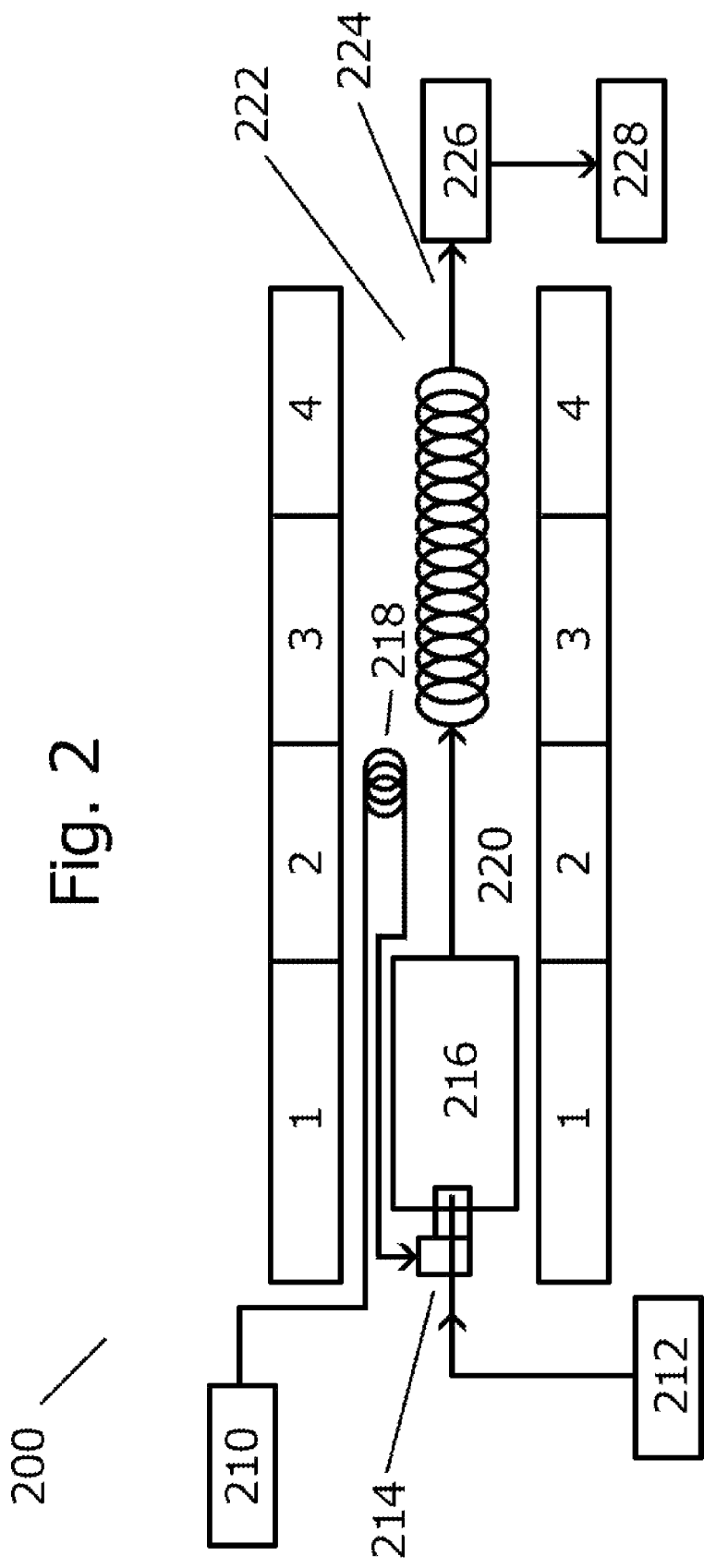
FIG. 2 illustrates the lab prototype potassium acetate vaporizer.

Promoted iron oxide catalysts are especially useful in the dehydrogenation of alkyl aromatic hydrocarbons to alkenyl aromatic hydrocarbons. For example, production of styrene by the dehydrogenation of ethylbenzene can be conducted by mixing ethylbenzene with steam, and passing the mixture through a dehydrogenation catalyst-packed bed. In many cases, compounds of an alkali metal, such as potassium, will be present in the dehydrogenation catalyst. The potassium can tend to diminish the deposition of coke on the catalyst during the dehydrogenation, and thereby increase the useful life of the catalyst. In an aspect, the potassium may be present typically in a quantity of at least 0.01 mole per mole iron oxide up to 1 mole per mole iron oxide. One embodiment of a dehydrogenation catalyst contains from 30 wt % to 95 wt % iron oxide and 1 wt % to 30 wt % of potassium. Another embodiment of a dehydrogenation catalyst contains from 40 wt % to 80 wt % iron oxide and 5 wt % to 20 wt % potassium. Other components may also be added to the dehydrogenation catalyst to provide further promotion, activation, or stabilization characteristics.

The dehydrogenation of ethylbenzene is usually carried out in the presence of steam, with the weight ratio of steam:ethylbenzene being from 0.5:1 to 4:1, or alternatively from 0.8:1 to 2:1. The steam can serve as a heat transfer medium, and can also stabilize an intermediate oxidation stage of the catalyst and aid in the gasification of any organic deposits on the catalyst, thus countering carbonization of the catalyst. A portion of the organic deposits can be oxidized into carbon monoxide and/or carbon dioxide.

After a fresh load of catalyst or the regeneration of an existing catalyst, there is typically an initial period of high catalyst activity and selectivity followed by catalyst deactivation. There are a number of possible explanations for the gradual deterioration of catalyst activity and one or more mechanisms may apply in a particular process. One mechanism that may deactivate alkali metal promoted iron-based catalysts is alkali metal loss, wherein the alkali metal is physically released from the catalyst and becomes entrained with the reactant stream. Another mechanism that may deactivate alkali metal promoted iron-based catalysts is alkali metal site contamination, that is, the physical location of the alkali metal on the catalyst is covered or otherwise obstructed, such as by carbonization. As catalyst deactivation progresses, eventually the level of conversion or selectivity, or both, fall sufficiently low that the dehydrogenation process is no longer economically viable. At this point the process would typically have to be shut down and the catalyst either replaced or regenerated by conventional methods.

Embodiments of the present invention involve adding an amount of alkali metal compound to the process sufficient to regenerate, stabilize, or enhance the activity of the dehydrogenation catalyst and thereby maintain economical levels of conversion and selectivity and reduce or delay the need for catalyst replacement. The alkali metal compound is added to a steam input stream prior to it entering the process. The alkali metal compound can be added in a continuous or intermittent basis as needed and can be utilized in conjunction with other operational techniques such as raising the reaction temperature mentioned above. In one embodiment the alkali metal compound is a potassium compound. In one embodiment the alkali metal compound is a potassium salt compound that can go into solution with the steam. In alternate embodiments the alkali metal compound is a lithium compound, a sodium compound, a rubidium compound, a cesium compound, a francium compound, mixtures thereof, and salts thereof.

Various embodiments and aspects of the present invention are given herein. The various aspects are generally not exclusive of each other and can be used in combination with each other.

In one embodiment the alkali metal compound that is added is an organo potassium salt. A soluble organo potassium salt is put into solution with steam before being added to the dehydrogenation process. A potassium salt can be sprayed or otherwise distributed into a stream of steam, for example super heated steam, which can dissolve and/or vaporize the salt and create a steam solution containing the potassium that can then be added to the dehydrogenation process. Organo potassium salts can vaporize at lower temperatures than non-organo potassium compounds, thereby facilitating the distribution of potassium into the flow of steam that is added to the dehydrogenation process. Various ways of putting a salt compound into solution with a liquid or vapor stream are well known in the art, all of which are considered within the scope of this invention. Non-limiting examples of suitable organo potassium salts include potassium acetate, potassium benzoate, potassium citrate, potassium fumarate, potassium gluconate, potassium lactate, potassium maleate, potassium pamoate, potassium succinate, potassium tartrate, and mixtures thereof. Potassium salt compounds generally have excellent water solubility, due to the high hydration energy of the K+ ion.

The amount of alkali metal compound added is dependent upon various factors such as the amount and purity of the reactant stream, the quantity of catalyst charge, the run length of the catalyst load, the dehydrogenation operating conditions, and the particular catalyst being treated. The alkali metal compound can be added in a substantially continuous manner, such as in an amount equivalent to a continuous addition of from 0.01 to 1000 parts per million by weight of alkali metal relative to the weight of the total reactant stream. In alternate embodiments the alkali metal compound is added in an amount equivalent to a continuous addition of 0.01 to 750; 0.10 to 500; or 0.1 to 250 parts per million by weight of alkali metal relative to the weight of the total reactant stream. In some embodiments the alkali metal compound is added in an amount equivalent to a continuous addition of 0.1 to 100 parts per million by weight of alkali metal relative to the weight of the total reactant stream. U.S. Pat. No. 6,936,743 to Butler, which is incorporated herein by reference, discloses the addition of a catalyst life extender in amounts equivalent to a continuous addition of from 0.01 to 100 parts per million by weight of the total alkyl aromatic hydrocarbon directed into the reactor.

The alkali metal compound can also be added in an intermittent manner, and intermittent addition may be desirable if the amount that is added is so small as to make continuous addition problematic. In some instances an intermittent addition of a larger quantity of alkali metal compound may provide superior results than a continuous addition of a smaller quantity. In alternate embodiments the alkali metal compound is added on an intermittent basis in an amount from 0.1 to 10,000 or more; 1.0 to 5000; or 100 to 1000 parts per million by weight of alkali metal relative to the weight of the reactant stream. Variations of the quantity and manner in which the alkali metal compound are added are considered within the scope of this invention.

An aspect of the present invention involves the transporting of an alkali metal solution to at least one process/apparatus within a plant. The alkali metal solution is prepared in a remote location. The first and second conduit and mixing chamber are remote from the fourth conduit and other apparatus/processes in a plant. The third conduit serves to transport the alkali metal solution from the remote location to the fourth conduit and optionally to other apparatus/processes. A fifth, and optionally sixth, conduit can divert at least a portion of the alkali solution to the other apparatus/processes. In an aspect, 10 to 90 percent of the alkali solution is diverted to the other apparatus/processes. In another aspect, 25 to 75 percent of the alkali solution is diverted to the other apparatus/processes. In an embodiment, the alkali solution is simultaneously delivered to the fourth conduit and to the other apparatus/processes.

The alkali metal solution may contain from 1 wt % to 95 wt % of an alkali metal salt. In another aspect, the alkali metal solution may contain from 5 wt % to 80 wt %, alternately from 5 wt % to 55 wt % or from 5 wt % to 40 wt % of an alkali metal salt, or alternately from 10 wt % to 30 wt % of an alkali metal salt. In a more specific aspect, the alkali metal salt includes potassium acetate that can be in solution with water, methanol or other material that enables the potassium acetate solution to be pumpable without decomposition. In an embodiment, the alkali metal solution is a potassium acetate solution having from 1 wt % to 95 wt % potassium acetate, alternately from 5 wt % to 80 wt %, 5 wt % to 55 wt %, 5 wt % to 40 wt % potassium acetate, or alternately from 10 wt % to 25 wt % potassium acetate.

In an embodiment, the alkali metal solution is first mixed with steam and then the mixture is fed to a vaporizer. In another embodiment, the alkali metal solution and steam are separately and independently fed to a vaporizer. The vaporizer may be heated by the steam feed itself and optionally from an additional heat source, such as a steam jacket or a heat exchanger. The vaporizer may be operated at temperatures ranging from 150° C. to 480° C. In another embodiment, the vaporizer is operated at temperatures ranging from 200° C. to 400° C. The ratio of salt solution fed to the vaporizer to steam fed to the vaporizer may be of from 1:3 salt solution to steam to 3:1 salt solution to steam.

In an aspect, alone or in combination with other aspects, a heat source is connected to the mixing chamber of the second conduit and to the third conduit and the heat source is selected from one or more of the group consisting of a steam jacket, electric heating element, and a radiative heat source.

Yet another embodiment is a method of revamping an existing facility used for the dehydrogenation of ethylbenzene to make styrene utilizing a potassium promoted iron based catalyst. The method involves adding an apparatus to a steam input stream for vaporizing an alkali metal salt into the steam input stream. The apparatus has a first conduit capable of transporting an alkali metal salt, the first conduit having at least one opening through which the alkali metal salt can exit the first conduit. A second conduit is in fluid communication with the first conduit, wherein the second conduit is capable of transporting a steam input stream. As the alkali metal salt exits the first conduit it is heated and simultaneously dissipated into the steam input stream forming a third stream containing vaporized alkali metal salt in solution with the steam. The portion of the first conduit containing the opening can be disposed within the second conduit in a substantially concentric arrangement. The apparatus may have at least one diffuser located adjacent to the opening of the first conduit to dissipate the first stream into the second stream. The third stream is sent to a third conduit in fluid communication with the second conduit. The third conduit is subject to a heat source. The third conduit of the apparatus may be connected to a fourth conduit for transporting the third stream into contact with a fourth stream within the fourth conduit and can further include a weir located adjacent to the connection of the third conduit to the fourth conduit to restrict the flow of any of the alkali metal that is not dissipated into the second stream from entering the fourth conduit.

Referring now to FIG. 1, in one illustrative embodiment 100 an alkali metal salt is supplied via a first conduit, line 110, and is added to an input stream of steam via a second conduit, line 120, where they are combined in a mixing chamber 130 prior to the mixture being transported down a third conduit, line 170, and subsequently added to a fourth conduit, the dehydrogenation process/apparatus 140. The dehydrogenation process 140 shown herein can be an input stream to a dehydrogenation process or can be a portion of the dehydrogenation apparatus, such as a dehydrogenation reaction zone. The alkali metal salt can be added as a liquid solution, as a solid, or in a vapor phase, or combinations thereof. In an aspect, the steam may be super heated. There may also be various mixing or agitating equipment employed within the mixing chamber 130 to facilitate the dissolution of the alkali metal salt into the steam. In an aspect, the mixing chamber 130 has a substantially concentric arrangement of the alkali metal salt line 110 within the steam line 120, with the streams from the salt line and the steam line contacting in a con-current flow pattern as shown in FIG. 1. In an alternative embodiment, the mixing chamber 130 has a concentric arrangement of the alkali metal salt line 110 within the steam line 120 with the streams from the salt line and the steam line contacting in a counter-current flow pattern, or with the alkali metal salt being sprayed or otherwise distributed within the mixing chamber 130. The alkali metal salt line 110 can alternately be attached at an any angle relative to the mixing chamber 130, such as from zero degrees on one embodiment having a con-current flow arrangement to 180 degrees on one embodiment having a counter-current arrangement, or alternatively on a 30 degree to 45 degree angle, or may be perpendicular to the mixing chamber 130 with the alkali metal salt being sprayed or otherwise distributed through an injector head. In an aspect, mixing chamber 130 is subjected to a heat source 180. Heat source 180 can include a steam jacket or an electrical heating element.

In the embodiment shown in FIG. 1, there is shown an optional diffuser 150 that can be used to dissipate the alkali metal salt within the steam stream in the mixing chamber 130. As used herein the term "diffuser" means any apparatus that acts to alter the flow path of the alkali metal salt to assist in its dissipation within the steam. The diffuser may decelerate the rate of flow, impart turbulence within the flow and/or impart a change in direction of the flow, or a combination thereof. The optional diffuser 150 may be of any shape to assist in dissipating the alkali metal salt within the steam stream. The diffuser may have an angled or conical shape, such as shown in FIG. 1, to deflect and distribute the alkali metal salt in a radial direction within the steam stream.

In an aspect, line 170 is subjected to a heat source 182. Heat source 182 can include a steam jacket or an electrical heating element. In an embodiment, this transport line, line 170, is heated at temperatures ranging from 200° C. to 400° C. In an optional embodiment, a fifth conduit and a sixth conduit, lines 190($a,b$), are used to transport at least a portion of the mixture in line 170 to another process/apparatus within a plant. There is also shown an optional weir 160 that can be used to restrict the flow of any alkali metal salt that is not in solution with the steam from entering the dehydrogenation process/apparatus 140. As used herein the term "weir" means any apparatus that restricts the flow of any alkali metal salt that is not in solution with the steam from entering the dehydrogenation process. The weir may inhibit the rate of flow of a portion of the flow that may contain alkali metal salt that is not fully in solution, such as in one embodiment the lower portion of the flow stream where heavier materials, such as alkali metal salt that is not in solution may settle. The mixture of alkali metal salt and steam can be added directly to a dehydrogenation reactor or to an input stream of the dehydrogenation process. Other ways of adding the alkali metal to the steam can include the heating and vaporizing of the alkali metal salt into the steam stream.

Dehydrogenation catalysts containing iron oxide and alkali metal compounds are well known in the art and are available commercially from various sources such as: BASF Corporation; Criterion Catalyst Company, L.P.; and Sud Chemie, Inc. These and similar catalysts are considered within the scope of this invention.

EXAMPLES

The embodiments having been generally described, the following examples are given as particular embodiments of the disclosure and to demonstrate the practice and advantages thereof. It is understood that the examples are given by way of illustration and are not intended to limit the specification or the claims in any manner.

A lab prototype of a potassium acetate vaporizer used for injection of the potassium acetate into a styrene catalyst feed has been constructed and used to evaluate process conditions. This prototype design incorporates the injection of a liquid potassium salt solution into a concurrent flow of steam at the inlet of a relatively large vessel. Transport of the vaporized potassium salt stream was simulated by attaching a length of heated tubing to the outlet of the vaporizer. The effluent was collected and gravimetrically evaluated for salt recovery. Suitable temperature ranges were developed for the vaporizer and the transport tube for both 10 and 25% potassium acetate solutions.

An embodiment of the lab prototype potassium acetate vaporizer system 200 is shown in FIG. 2. Water 210 and potassium acetate solution 212 were added to the system 200 using continuous-flow dual syringe pumps. The body 216 was a 75 mL pressure sample vessel with ¼-inch LPT fittings on each end. The inlet was a bored-through "T" fitting 214 with a ⅟₁₆-inch tube inserted through to the edge of the fitting inside the body 216 for addition of the potassium acetate solution. Water was pumped into coiled tubing 218 that was inside the furnace to create the diluent stream that was then introduced to the "T" fitting 214 behind the potassium acetate introduction. The vaporizer effluent was sent through a transport tube 220 that is of 3 feet in length of ¼-inch tubing that has been spiral-coiled 222. The vaporizer 216 and transport tube 220, 222 were located inside a 4-zone furnace. The first zone 1 housed the vaporizer vessel while the other three zones 2, 3, 4 contained the transport tube 220, 222. Zone 1 was separated from zones 2-4 by a plug of insulation. The transport tube 224 that left the furnace was connected to a chilled water condenser 226. A collection bottle 228 was attached to the condenser 226 to collect the liquid product.

The vaporizer experiments began by heating the vaporizer and transport tube to the desired temperatures and then introducing the water for the steam. Once steady temperatures were achieved, the potassium acetate addition started; this was the start time for the experiment. The experiments lasted for 2-4 hours with total collection of the liquid effluent into a tared bottle. The liquid was sampled for chemical analysis. Then the solution was evaporated in a drying oven to obtain the amount of potassium acetate. An Inductively Coupled Plasma (ICP) analysis was used to confirm the salt quantity. The experimental data are shown in Table 1 below.

TABLE 1

Vaporization Data using a Transfer Line and Condenser

| Data | Vaporizer Temp (° C.) | Vaporizer Temp (° F.) | Transtube Temp (° C.) | Salt Weight Percent | Salt Solution (mL/min) | Carrier Steam (mL/min) | Time (min) | Salt Collected (g) | Salt Theoretical (g) | Percent Yield |
|---|---|---|---|---|---|---|---|---|---|---|
| Sep. 4, 2008 | 400 | 752 | 200 | 10 | 2 | 2 | 240 | 29.82 | 50.11 | 59.51 |
| Sep. 4, 2008 | 450 | 842 | 200 | 10 | 2 | 2 | 173 | 36.32 | 36.12 | 100.55 |
| Sep. 5, 2008 | 450 | 842 | 200 | 10 | 2 | 2 | 135 | 28.84 | 28.19 | 102.31 |
| Sep. 5, 2008 | 465 | 869 | 200 | 10 | 2 | 2 | 130 | 24.44 | 27.14 | 90.04 |
| Sep. 8, 2008 | 475 | 887 | 200 | 10 | 2 | 2 | 146 | 29.68 | 30.48 | 97.36 |
| Sep. 8, 2008 | 485 | 905 | 200 | 10 | 2 | 2 | 136 | 26.69 | 28.40 | 93.99 |
| Sep. 9, 2008 | 495 | 923 | 200 | 10 | 2 | 2 | 154 | 28.84 | 32.16 | 89.69 |
| Sep. 9, 2008 | 505 | 941 | 200 | 10 | 2 | 2 | 195 | 28.8 | 40.72 | 70.73 |
| Sep. 12, 2008 | 515 | 959 | 200 | 10 | 2 | 2 | 131 | 11.06 | 27.35 | 40.43 |
| Sep. 12, 2008 | 525 | 977 | 200 | 10 | 2 | 2 | 120 | 46.19 | 25.06 | 184.35 |
| Sep. 23, 2008 | 515 | 959 | 200 | 10 | 2 | 2 | 150 | 11.35 | 31.32 | 36.24 |
| Sep. 27, 2008 | 460 | 860 | 200 | 10 | 2 | 2 | 180 | 34.49 | 37.58 | 91.77 |
| Sep. 27, 2008 | 470 | 878 | 200 | 10 | 2 | 2 | 138 | 26.49 | 28.81 | 91.93 |
| Sep. 29, 2008 | 490 | 914 | 200 | 10 | 2 | 2 | 127 | 20.43 | 26.52 | 77.04 |
| Sep. 29, 2008 | 495 | 923 | 200 | 10 | 2 | 2 | 142 | 18.22 | 29.65 | 61.45 |
| Sep. 29, 2008 | 505 | 941 | 200 | 10 | 2 | 2 | 131 | 22.69 | 27.35 | 82.95 |
| Oct. 1, 2008 | 455 | 857 | 200 | 10 | 2 | 2 | 136 | 30.57 | 28.40 | 107.65 |
| Oct. 1, 2008 | 475 | 887 | 200 | 10 | 2 | 2 | 137 | 28.26 | 28.61 | 98.79 |
| Oct. 3, 2008 | 390 | 734 | 200 | 10 | 2 | 2 | 129 | 29.67 | 26.94 | 110.15 |
| Oct. 3, 2008 | 380 | 716 | 200 | 10 | 2 | 2 | 123 | 24.39 | 25.68 | 94.97 |
| Oct. 4, 2008 | 370 | 698 | 200 | 10 | 2 | 2 | 120 | 25.41 | 25.06 | 101.41 |
| Oct. 4, 2008 | 360 | 680 | 200 | 10 | 2 | 2 | 122 | 24.19 | 25.47 | 94.96 |
| Oct. 4, 2008 | 350 | 662 | 200 | 10 | 2 | 2 | 122 | 24.08 | 25.47 | 94.53 |
| Oct. 6, 2008 | 455 | 857 | 200 | 10 | 2 | 2 | 140 | 27.88 | 29.23 | 95.37 |
| Oct. 6, 2008 | 490 | 914 | 200 | 10 | 2 | 2 | 129 | 21.16 | 26.94 | 78.56 |
| Oct. 7, 2008 | 340 | 644 | 200 | 10 | 2 | 2 | 122 | 25.68 | 25.47 | 100.81 |
| Oct. 8, 2008 | 425 | 797 | 200 | 10 | 2 | 2 | 123 | 24.29 | 25.68 | 94.58 |
| Oct. 8, 2008 | 340 | 644 | 200 | 10 | 2 | 2 | 121 | 24.05 | 25.26 | 95.19 |
| Oct. 9, 2008 | 330 | 626 | 200 | 10 | 2 | 2 | 125 | 26.06 | 26.10 | 99.85 |
| Oct. 9, 2008 | 320 | 608 | 200 | 10 | 2 | 2 | 141 | 28.26 | 29.44 | 95.99 |
| Oct. 11, 2008 | 200 | 392 | 200 | 10 | 2 | 2 | 123 | 24.95 | 25.68 | 97.15 |
| Oct. 11, 2008 | 200 | 392 | 200 | 10 | 2 | 2 | 124 | 24.5 | 25.89 | 94.63 |
| Oct. 11, 2008 | 200 | 392 | 200 | 10 | 2 | 2 | 120 | 23.77 | 25.06 | 94.87 |
| Oct. 16, 2008 | 500 | 932 | 200 | 10 | 1 | 2 | 198 | 9.67 | 20.67 | 46.78 |
| Oct. 20, 2008 | 500 | 932 | 200 | 10 | 1 | 3 | 127 | 0 | 13.26 | 0.00 |
| Oct. 21, 2008 | 450 | 842 | 200 | 10 | 1 | 1 | 428 | 39.4 | 44.68 | 88.18 |
| Oct. 28, 2008 | 180 | 356 | 200 | 10 | 2 | 2 | 146 | 3.33 | 30.48 | 10.92 |
| Nov. 2, 2008 | 350 | 662 | 200 | 25 | 2 | 2 | 120 | 64.54 | 62.64 | 103.03 |
| Nov. 2, 2008 | 400 | 752 | 200 | 25 | 2 | 2 | 124 | 69.33 | 64.73 | 107.11 |
| Nov. 2, 2008 | 450 | 842 | 200 | 25 | 2 | 2 | 126 | 66.65 | 65.77 | 101.33 |
| Nov. 11, 2008 | 400 | 752 | 200 | 10 | 2 | 2 | 152 | 39.06 | 31.74 | 112.31 |
| Nov. 15, 2008 | 400 | 752 | 200 | 10 | 2 | 2 | 142 | 28.14 | 29.65 | 94.91 |
| Dec. 9, 2008 | 200 | 392 | 200 | 10 | 1 | 3 | 141 | 16.73 | 14.72 | 113.65 |
| Dec. 10, 2008 | 180 | 356 | 200 | 10 | 1 | 3 | 230 | 25.75 | 24.01 | 107.24 |
| Dec. 10, 2008 | 170 | 338 | 200 | 10 | 1 | 3 | 181 | 19.67 | 18.90 | 104.09 |
| Dec. 11, 2008 | 160 | 320 | 200 | 10 | 1 | 3 | 137 | 13.99 | 14.30 | 97.81 |
| Dec. 12, 2008 | 150 | 302 | 200 | 10 | 1 | 3 | 135 | 13.73 | 14.09 | 97.42 |
| Jan. 29, 2008 | 200 | 392 | 200 | 25 | 2 | 2 | 164 | 89.43 | 85.608 | 104.46 |
| Jan. 29, 2008 | 200 | 392 | 200 | 25 | 1 | 3 | 110 | 29.46 | 28.71 | 102.61 |
| Feb. 3, 2008 | 175 | 347 | 200 | 25 | 1 | 3 | 182 | 49.61 | 47.50 | 104.44 |
| Feb. 3, 2008 | 150 | 302 | 200 | 25 | 1 | 3 | 123 | 32.29 | 32.10 | 100.58 |

Example 1

A variety of vaporizer temperatures were conducted to determine an effective operating range for the vaporization of potassium acetate. Most of the experiments were conducted with a 2 mL/min flow of water for the carrier steam and 2 mL/min of potassium acetate solution. The potassium acetate solution was injected into the carrier steam at the inlet of the vaporizer and the stream is condensed and collected at the outlet. The collected effluent solution was evaporated in a drying oven. The recovered salt was weighed and compared with the theoretical amount expected.

Figure 3:
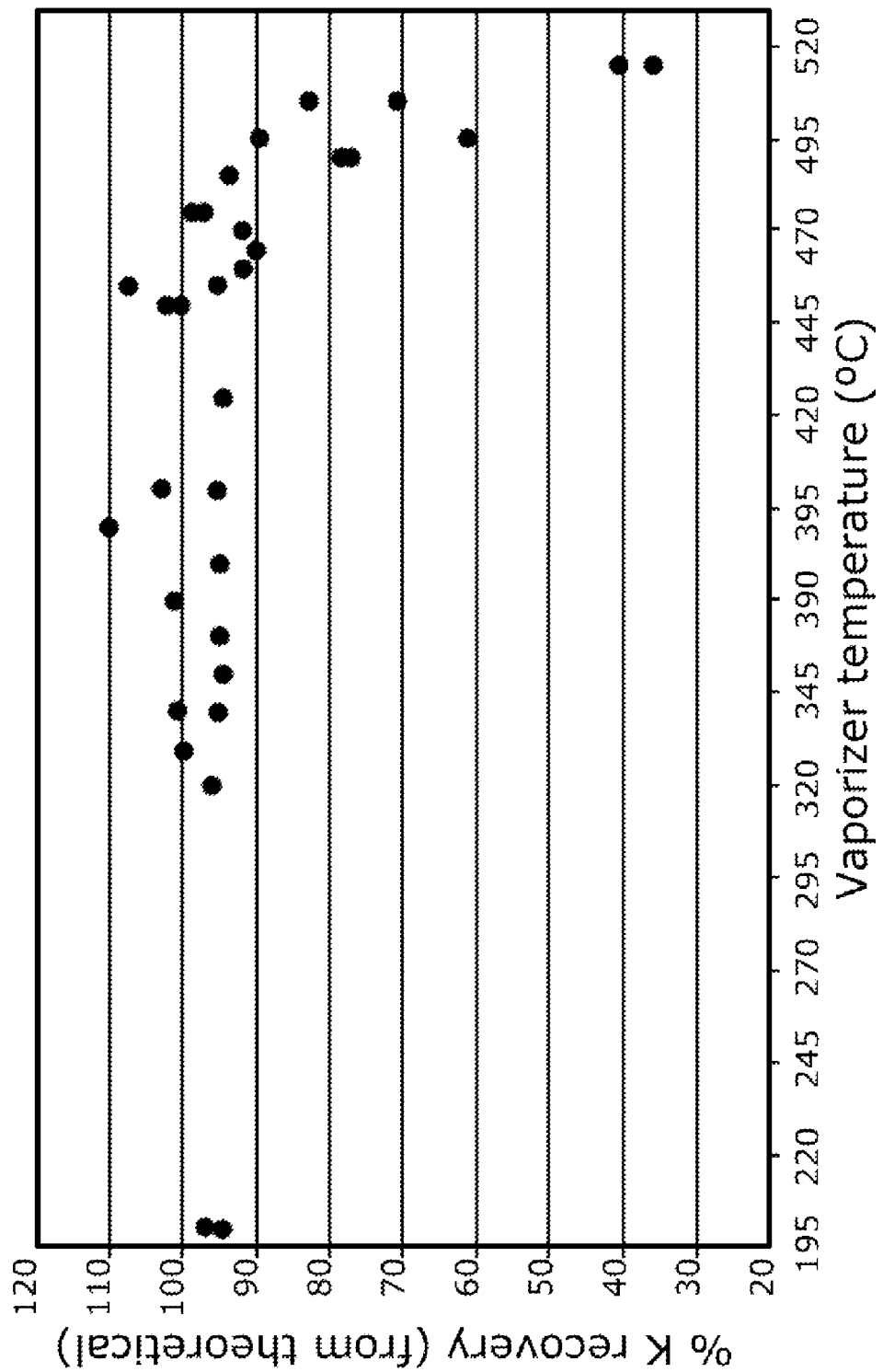
FIG. 3 is a plot of potassium acetate recovery versus the vaporizer temperature using 2 mL/min water for steam and 2 mL/min of 10% potassium acetate.

FIG. 3 shows the results for the investigation of viable vaporizer operating temperatures for a 10% potassium acetate solution. Potassium acetate recovery was used as the critical measurement. A successful experiment would show 100% potassium acetate recovery. Lower recovery numbers indicate that the potassium acetate was deposited in the apparatus and not fully entrained in the vapor phase. The safe operating range is from 200-480° C. using 10% potassium acetate. Above 480° C., the potassium acetate is not thermally stable, thereby leading to the formation of KOH and $K_2CO_3$ and deposition. Below 200° C., the vapor pressure of potassium acetate may be too low or there is insufficient heat for vaporization.

The transfer tube was heated by different furnace zones than those used by the vaporizer. Testing of earlier versions of the vaporizer system was conducted with a transfer tube temperature at 400° C. initially. The lowering of the transfer tube temperature to 200° C. resulted in no changes in salt recovery results. The 200° C. transfer tube temperature was employed for all remaining testing as shown in Table 1.

Figure 4:
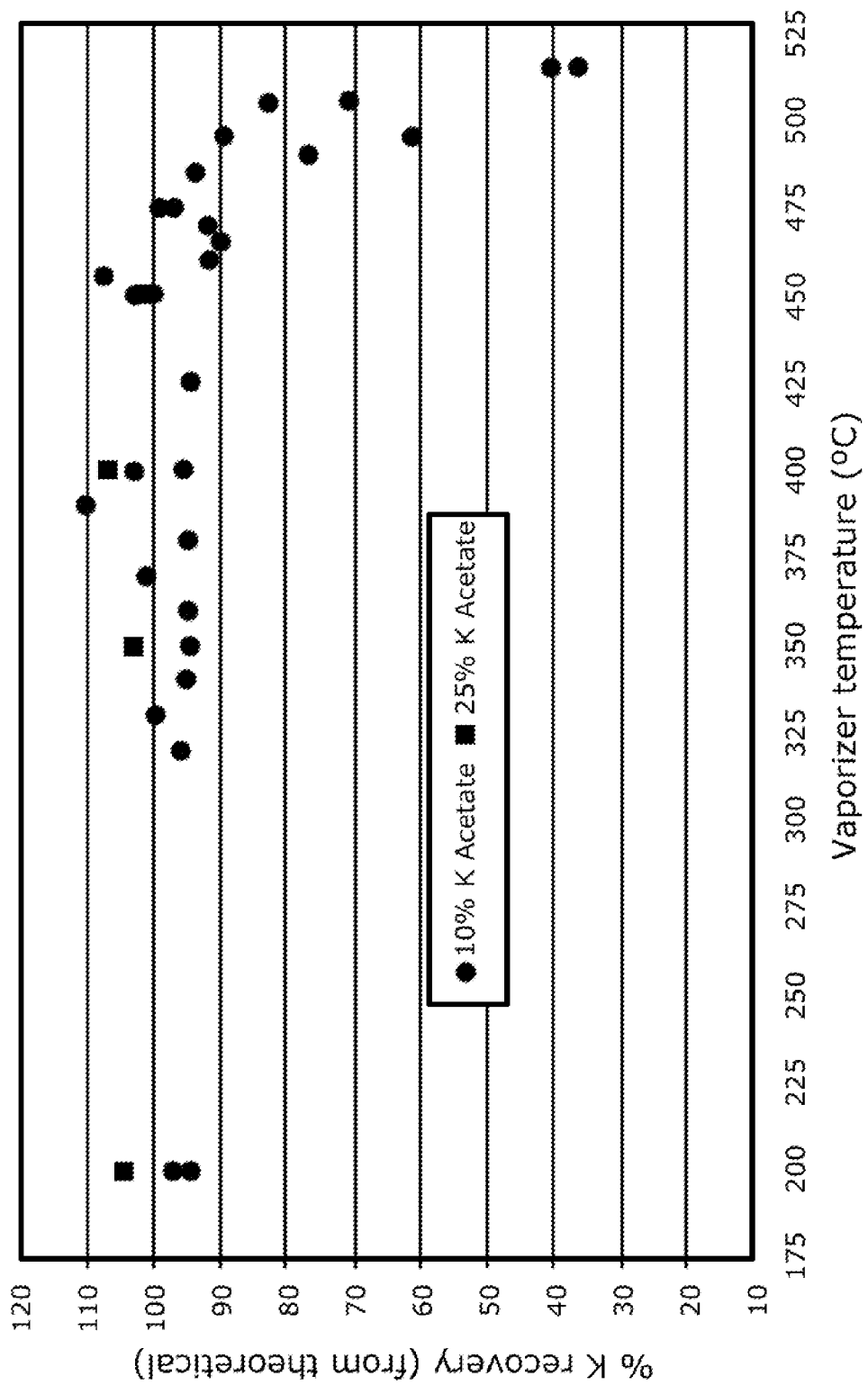
FIG. 4 is a plot of potassium acetate recovery versus the vaporizer temperature using 2 mL/min water for steam and 2 mL/min of 25% potassium acetate compared with the 10% potassium acetate data of FIG. 3.

The use of high concentration potassium acetate solution may bring benefits in capital and the operational costs of a vaporizer. For those reasons, a 25% potassium acetate solution was used in the vaporizer. FIG. 4 shows the results of the 25% potassium acetate solution overlaid with those of the 10% solution. The 25% potassium acetate can be used over this same operational range as the 10% solution.

On a weight basis, there was only 5 wt % potassium acetate in the effluent of the 2 mL/min water and 2 mL/min 10% potassium acetate experiment. This amounted to only about 2% K correcting for the acetate ion. On a molar basis, the effluent contained less than 1 mol % K due to the molecular weight differences. For the corresponding 25% potassium acetate experiments, the corresponding numbers were 12.5 wt % potassium acetate or 5 wt % K in the effluent. The K molar percent was about 2.5%, also. The molar percentages of potassium acetate in the gas phase correlates directly with the partial pressure so the vaporizer will show a very low partial pressure of potassium acetate, which should help the vaporization process.

Example 2

Figure 5:
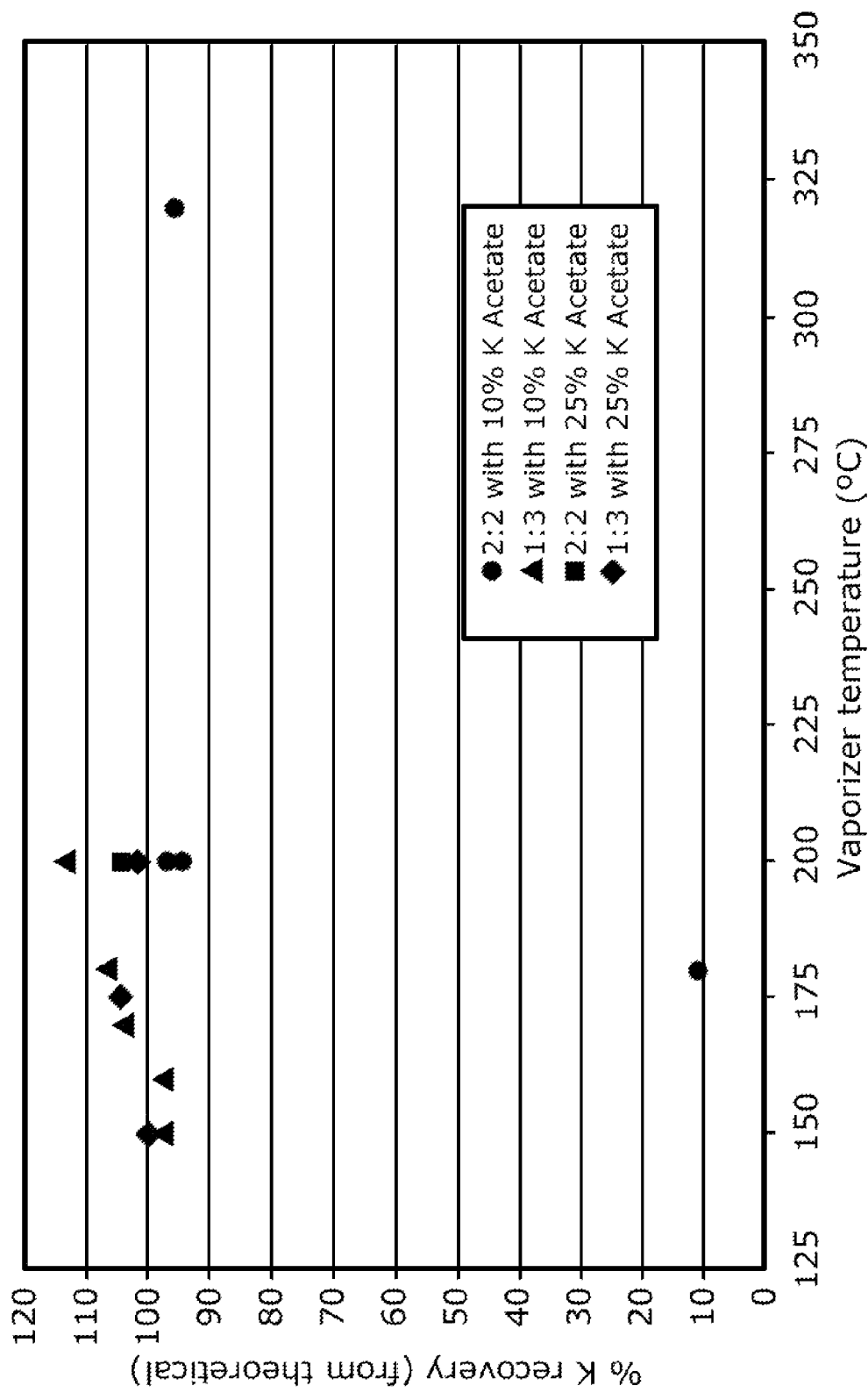
FIG. 5 is a plot of an expanded lower temperature limit using 3 mL/min water with 1 mL/min potassium acetate solutions.

Other experiments were conducted with higher water flows and lower potassium acetate flows than that of Example 1. These experiments were done for both 10% and 25% potassium acetate. The water was increased to 3 mL/min and the potassium acetate solution decreased to 1 mL/min. This maintained the total flow to the vaporizer, but with different feed ratios. This data is shown in FIG. 5. The higher ratio of steam to potassium acetate solution allowed the successful vaporization at 150° C. for both 10% and 25% potassium acetate.

As used herein, the term "conversion" means in a quantitative sense the fraction, in % mole, of the reactant that is converted.

The term "selectivity" means the ability of the catalyst to selectively produce higher levels of a desirable product and lower levels of an undesirable product, for example to selectively dehydrogenate ethylbenzene to produce styrene instead of toluene or benzene.

The term "activity" means the ability of the catalyst to convert a certain percentage of the reactants for each pass of feedstock over the catalyst, for example to convert a certain percentage of the ethylbenzene to aromatics for each pass of feedstock over the catalyst.

Depending on the context, all references herein to the "invention" may in some cases refer to certain specific embodiments only. In other cases it may refer to subject matter recited in one or more, but not necessarily all, of the claims. While the foregoing is directed to embodiments, versions and examples of the present invention, which are included to enable a person of ordinary skill in the art to make and use the inventions when the information in this patent is combined with available information and technology, the inventions are not limited to only these particular embodiments, versions and examples. Other and further embodiments, versions and examples of the invention may be devised without departing from the basic scope thereof and the scope thereof is determined by the claims that follow.

What is claimed is:

1. A method of enhancing the activity of a dehydrogenation catalyst promoted with an alkali metal during a catalytic dehydrogenation reaction, comprising:
    forming a first solution by adding an alkali metal salt to steam utilizing an apparatus;
    the apparatus having a first conduit that transports a first stream of an alkali metal salt, the first conduit having at least one opening through which the first stream exits the first conduit;
    the apparatus having a second conduit in fluid communication with the first conduit, wherein the second conduit transports a second stream comprising steam, wherein as the first stream exits the first conduit it is dissipated into the second stream forming the first solution containing alkali metal salt of the first stream in solution with the steam of the second stream;
    the apparatus having a third conduit in fluid communication with the second conduit, wherein the third conduit transports the first solution, and is capable of being heated by a heat source; and
    bringing the first solution into contact with a dehydrogenation catalyst.

2. The method of claim 1, wherein the alkali metal salt is added in amounts sufficient to maintain substantially constant levels of catalyst activity.

3. The method of claim 1, wherein the alkali metal salt is a potassium salt compound.

4. The method of claim 1, wherein the catalytic dehydrogenation reaction is the dehydrogenation of an alkyl aromatic hydrocarbon reactant stream to obtain an alkenyl aromatic hydrocarbon.

5. The method of claim 1, wherein the alkali metal salt is added to the second stream as a solid.

6. The method of claim 1, wherein the alkali metal salt is added to the second stream as a liquid.

7. The method of claim 1, wherein the alkali metal salt is added to the second stream as a vapor.

8. The method of claim 1, wherein the dehydrogenation catalyst comprises 40-80 wt % iron oxide and 5-30 wt % alkali metal compound.

9. The method of claim 1, wherein the alkali metal salt added is equivalent to a continuous addition of from 0.01 to 1000 parts per million by weight of alkali metal relative to the weight of a total reactant stream contacting the dehydrogenation catalyst.

10. The method of claim 1, wherein the alkyl aromatic hydrocarbon is ethylbenzene and the alkenyl aromatic hydrocarbon is styrene.

11. The method of claim 1, further comprising heating the second conduit, the third conduit, or both.

12. The method of claim 1, further comprising:
providing a portion of the first solution from the third conduit to a fourth conduit;
bringing the portion of the first solution into contact with the dehydrogenation catalyst in the fourth conduit; and
diverting at least a portion of the first solution from the third conduit into a fifth conduit and optionally into a sixth conduit in fluid communication with the third conduit.

13. The method of claim 1, wherein a ratio of alkali metal salt to steam ranges from 1:3 to 3:1.

14. A method of vaporizing and transporting an alkali metal salt comprising:
providing a first stream comprising an alkali metal salt to a first conduit;
wherein the first conduit transports the alkali metal salt and has at least one opening through which the alkali metal salt can exits the first conduit;
providing a second stream comprising steam to a second conduit that transports the steam and is in fluid communication with the first conduit;
wherein as the alkali metal salt exits the first conduit it is dissipated into the second stream forming a third stream containing alkali metal salt in solution with the steam;
providing the third stream to a third conduit in fluid communication with the second conduit, wherein the third conduit transports the third stream, wherein the third conduit is capable of being heated by a heat source.

15. The method of claim 14, wherein at least one diffuser located adjacent to the at least one opening of the first conduit is used to dissipate the first stream into the second stream.

16. The method of claim 14, wherein the third conduit of the apparatus is connected to a fourth conduit for transporting the third stream into contact with a fourth stream within the fourth conduit and further comprises a weir located adjacent to the connection of the third conduit to the fourth conduit to restrict the flow of any of the alkali metal that is not dissipated into the second stream from entering the fourth conduit.

17. The method of claim 14, further comprising heating the second conduit, the third conduit, or both.

18. The method of claim 14, wherein the second conduit is heated by a first heat source, the third conduit is heated by a second heat source, or both.

19. The method of claim 18, wherein each heat source comprises a steam jacket, a heat exchanger, an electrical heating element, a radiative heat source, or combinations thereof.

20. The method of claim 14, wherein the second conduit is heated to a temperature ranging from 150° C. to 480° C., wherein the third conduit is heated to a temperature ranging between 150° C. to 500° C., or both.

21. The method of claim 14, wherein the third conduit is subjected to an amount of heat sufficient to maintain the third stream in a fluid state.

22. The method of claim 14, further comprising:
providing a portion of the third stream from the third conduit to a fourth conduit;
bringing the portion of the third stream into contact with a dehydrogenation catalyst in the fourth conduit; and
diverting at least a portion of the third stream from the third conduit into a fifth conduit and optionally into a sixth conduit in fluid communication with the third conduit.

23. The method of claim 14, wherein a ratio of alkali metal salt to steam ranges from 1:3 to 3:1.

* * * * *